United States Patent [19]
Feiring

[11] Patent Number: 5,368,561
[45] Date of Patent: Nov. 29, 1994

[54] METHOD OF EFFECTING CATHETER EXCHANGE AND DEVICE FOR USE IN SAME

[75] Inventor: Andrew Feiring, Milwaukee, Wis.

[73] Assignee: Microvena Corporation, White Bear Lake, Minn.

[21] Appl. No.: 119,606

[22] Filed: Sep. 10, 1993

[51] Int. Cl.⁵ ............................................. A61M 31/00
[52] U.S. Cl. ....................................... 604/53; 604/164
[58] Field of Search ................... 128/772; 604/52, 53, 604/49, 164, 280

[56] References Cited

U.S. PATENT DOCUMENTS 4,826,481  5/1989  Sacks et al. ........................ 604/164
4,997,424  3/1991  Little ................................. 604/280
5,114,401  5/1992  Stuart et al. ......................... 604/53

FOREIGN PATENT DOCUMENTS 341830  11/1989  European Pat. Off. ............ 604/53
9207895  9/1992  WIPO .

Primary Examiner—John G. Weiss
Attorney, Agent, or Firm—Fredrikson & Byron

[57] ABSTRACT

The invention provides a method for effecting a catheter exchange by cutting a catheter perpendicularly to it's axis and maintaining a grip on a guidewire while the cut end of the catheter is withdrawn rearwardly over the guidewire's distal end. This permits the operator to maintain the guidewire's position during the removal of the catheter.

8 Claims, 2 Drawing Sheets

METHOD OF EFFECTING CATHETER EXCHANGE AND DEVICE FOR USE IN SAME

FIELD OF THE INVENTION

The present invention generally relates to methods and apparatuses used in connection with medical catheters and particularly provides a method and apparatus useful in exchanging catheters in medical procedures.

BACKGROUND OF THE INVENTION

Guidewires are frequently used in medical procedures to direct medical implements to specific locations within a patient's body. Most commonly, guidewires are used to define a path to a desired location within a patient's vascular system and a second device, such as a catheter, tracks along the guidewire until it reaches the desired location. Frequently, the desired location for the medical device can be rather distant from the point of insertion of the guidewire into a patient's vascular system; distances of up to 175 cm are not uncommon.

In standard practice, a guidewire will be introduced into a patient's vascular system at a location remote of the site to be accessed and guided through the vascular system. This is normally accomplished by using a remotely steerable guidewire which permits the operator to select a specific path through a maze of branching passages until the desired location is reached. This process of guiding the guidewire can take a fairly long period of time for certain operations, such as accessing selective sites within coronary vessels.

Once a guidewire is in the patient's vascular system, a catheter or other similar device will often be placed over the guidewire and urged along the guidewire through the vascular system. In some procedures, the catheter is passed over the guidewire shortly after the guidewire is introduced, leaving only the steerable tip of the guidewire to extend beyond the end of the catheter, and the catheter and guidewire are advanced together. In other instances, only after the guidewire is guided to a desired location is the catheter placed over the guidewire, and the catheter is then urged along the guidewire until it reaches its destination.

In some instances, though, it may be necessary to remove the first catheter from the patient's body and replace it with a different catheter or some other intravascular medical device. For instance, in balloon catheterization procedures for enlarging stenosed lengths of vascular channels, a first balloon catheter having a relatively small balloon may be used first. Then the first catheter may be replaced with a series of catheters having successively larger balloons or differently shaped balloons to further enlarge the channel.

Ordinarily, guidewires are generally only a little longer than the catheters with which they are used. If one were to remove the catheter, there would be no way to grasp the guidewire to hold it in place during this removal because it would be completely enclosed within the catheter's lumen. Obviously, it would be preferable to keep the guidewire in position so that it will not have to be guided once again to its desired location. In the past, the guidewire was commonly replaced with a much longer wire before removing the catheter. This "exchange wire" was commonly about twice the length of the guidewire it replaced (e.g. about 260 cm or longer), permitting an operator to maintain a grasp on the wire as the catheter was removed. The catheter would then be removed from the exchange wire and the exchange wire would be used to guide the next catheter to the desired location.

Such exchange wires solved the basic problem of maintaining guidewire position during catheter exchanges, but they presented additional difficulties of their own. For instance, if a particularly selective guidewire position was needed, sometimes the precise desired position would be lost during the exchange of the initial guidewire—when replacing the guidewire, it had to be removed prior to introducing the exchange wire. Removing the guidewire for exchange could cause the operator to lose a precise position of the distal end of the guidewire.

In order to solve this problem, means for adding an extension to the proximal end of the initial guidewire have been developed. In general, such guidewire extensions involve affixing a second guide wire, which may be referred to as an extension wire, directly to the proximal end of the initial guidewire without requiring the initial wire to be moved. This helps overcome some of the difficulties of the prior art in that it allows the operator to leave the original guidewire in place yet maintain a grip on either the guidewire or the extension wire as the catheter is removed.

However, this solution also presents some difficulties of its own, such as making a secure connection between the guidewire and the extension wire when both of these wires tend to have rather small diameters so they can fit in the lumen of a vascular catheter. The extension wire must be carefully formed to mate with the end of the original guidewire, increasing the costs of each of these components. This solution also requires that the original guidewire be of a type designed to be used in a catheter exchange procedure and increases the equipment costs for the procedure as the guidewire and extension wires are generally intended to be disposed after a single use. Furthermore, the extended guidewire tends to be extremely long, e.g. on the order of 3 meters, and can be relatively cumbersome to handle effectively.

Others have proposed alternative solutions. For instance, an international patent application published under the Patent Cooperation Treaty in the name of Baxter International Inc. (International Publication Number WO 93/05814), teaches a catheter having two lumens, one of which is adapted to receive a guidewire. This small "sublumen" within the overall catheter lumen is provided with a fracture line which allows the catheter to be split lengthwise to expose the guidewire. By splitting open the catheter along this seam one can take the catheter off of the guidewire without necessitating the removal of the guidewire from a position in the patient's body.

However, the solution proposed by Baxter has a number of drawbacks of its own. For example, the catheter used by Baxter must be used initially by the person performing the procedure. In some instances, the need for a different catheter is not realized until the operator has a first catheter in place and realizes it will not perform adequately. Accordingly, if a catheter such as that taught by Baxter is not used initially, one must still face the difficulties noted above in exchanging a standard catheter.

SUMMARY OF THE INVENTION

The present invention provides a method and device for effecting a catheter exchange which can be used with virtually any catheter design. In accordance with the method, at least a portion of an elongate catheter carried about a guidewire is disposed within a patient's body, with a proximal length of the guidewire extending rearwardly beyond the proximal end of the catheter. The catheter is removed from the guidewire by cutting away a proximal length of the catheter, preferably by means of a cut oriented generally perpendicularly to the axis of the catheter and the guidewire.

The separated proximal length is then withdrawn rearwardly over the guidewire. The operator can maintain a grip on the guidewire during the entire procedure by alternating the location of the grip between a location adjacent the proximal end of the guidewire and a location adjacent where the catheter has been cut. This permits the operator to maintain the guidewire's position during the removal of the catheter.

The catheter can then be retracted rearwardly over the guidewire to a position wherein the proximal end of the remaining length of the catheter is positioned closer to the proximal end of the guidewire. The cutting and retracting procedure can then be repeated as many times as necessary to remove the entire catheter (if so desired) in a series of discrete proximal lengths. As catheters are contaminated by contact with a patient's bodily fluids and are therefore disposed after a single use, cutting the catheter into segments does not waste any valuable resources.

If so desired, a new catheter can then be placed over the guidewire and follow the guidewire to the desired location. In many (if not most) operations, a guidewire is much less likely to lose position when a new catheter is urged distally along the wire than when a catheter is being retracted proximally off of the guidewire. Accordingly, it will frequently be unnecessary to maintain a grip on the guidewire when introducing the new catheter.

In accordance with another embodiment of the invention, a catheter cutting device is provided and may be used in the procedure outlined above to cut the catheter. This catheter cutter is provided with at least one cutting orifice sized to cut through the catheter with the edges of the orifice yet leave sufficient room for the guidewire to be safely received in the orifice. In a preferred embodiment, the catheter cutter is provided with a plurality of such orifices defined by opposed notches in a pair of opposed jaws, with each such orifice so defined being differently sized.

The orifices are desirably adapted to present a range of sizes suitable for use with different catheter/guidewire combinations. In a further embodiment, the jaws of the cutter include visible indicia adjacent each orifice indicating at least the size of the guidewire which the orifice is sized to receive. As the operator will know the size of the guidewire being used in the procedure, the proper orifice can be easily and accurately selected.

DETAILED DESCRIPTION OF THE PREFERRED EMBODIMENTS

Figure 1:
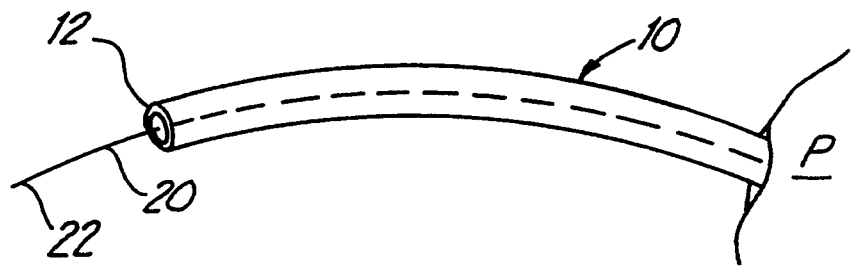
FIGS. 1-4 are a schematic illustration of a method of removing a catheter from about a guidewire in accordance with the present invention.
Figure 2:
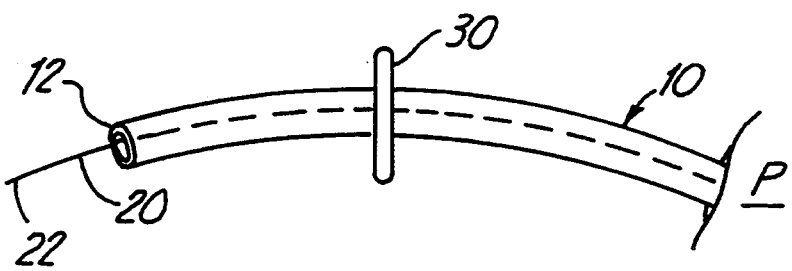

FIGS. 1-4 schematically illustrate a method of removing a catheter from about a guidewire in accordance with the present invention. Turning first to FIG. 1, a catheter 10 is carried about a guidewire 20 which is received inside the catheter's lumen. Both the catheter 10 and the guidewire 20 extend into the patient's body P, such as into the patient's vascular system. The guidewire extends proximally behind the proximal end of the catheter a sufficient distance to allow an operator to manually grasp the distal end 22 of the guidewire.

When the operator desires to remove the catheter 10 without losing the position of the guidewire 20 within the patient's body, he or she may first grasp the guidewire 20 at a location behind (i.e., proximally of) the proximal end 12 of the guidewire. For instance, the operator may grasp the guidewire adjacent its proximal end 22.

While grasping the guidewire 20 to hold it in place, the catheter 20 may be cut at a position disposed outside of the patient's body. This cut may be made in any fashion which will serve to sever a proximal portion of the catheter from the rest of the catheter. For instance, this may be accomplished by cutting the catheter with a scalpel or the like. Optimally, though, the cut is oriented generally perpendicularly to the axis of the guidewire.

In one particularly preferred embodiment, a catheter cutter 30 such as is described in detail below is used to cut the catheter. If such a catheter cutter 30 is employed, the properly sized cutting orifice is first selected. In the version of the cutter 30 set forth below, the cutter defines a plurality of cutting orifices having visible indicia associated with each orifice indicating the size of the orifice. Since the operator will know (or can readily determine) the size of the guidewire being used, the proper orifice can be selected simply by choosing the orifice bearing markings correlating the orifice to the size guidewire being used.

The catheter cutter 30 may then be used to cut through the catheter, but not the guidewire. Optimally, the orifice is sized to ensure a cut through substantially the entire thickness of the catheter's tubular wall without requiring any compressive forces of the cutter 30 on the guidewire. The process of using the cutter 30 to cut a catheter and the structure of the cutter 30 are detailed below.

Figure 3:
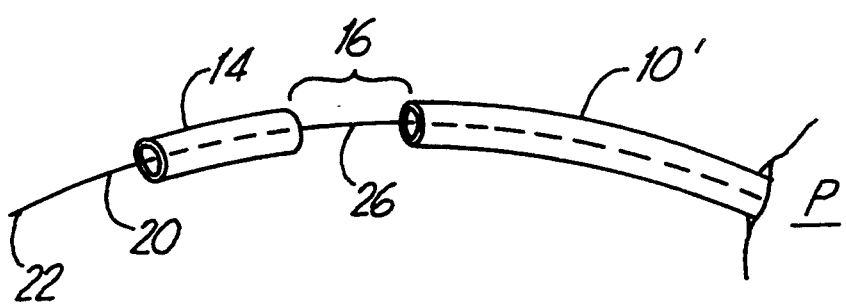

Cutting the catheter in this manner cuts away a proximal length 14 of the catheter, serving to divide the catheter into two discrete parts. As best seen in FIG. 3, the proximal length 14 of the catheter may be retracted proximally along the guidewire while maintaining a grip on the proximal end 22 of the guidewire. This will define a gap 16 between the severed proximal length and the main body of the shortened catheter 10'.

Once the gap 16 is sufficiently wide, the operator may grasp the guidewire exposed in this gap. Although the operator could let go of the proximal end of the guidewire before grasping the exposed length 26, to be certain that the guidewire will not be inadvertently moved the operator may instead grasp the exposed segment 26 before letting go of the proximal end of the guidewire in the other hand. The hand which previously held the proximal end 22 of the guidewire may then be used to withdraw the severed proximal length 14 of the catheter.

Figure 4:
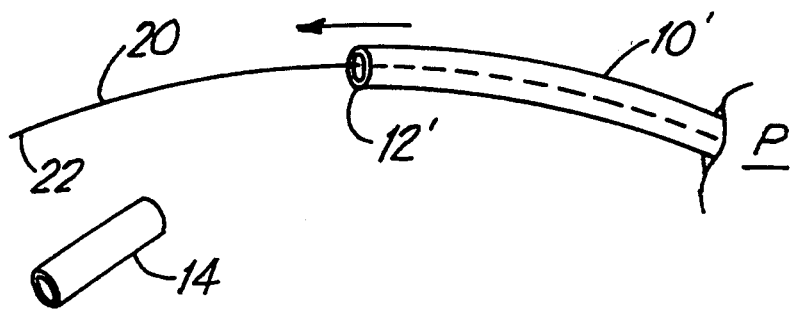

The proximal length 14 of the catheter can continue to be moved proximally along the guidewire 20 until it is removed from the wire. As schematically illustrated in FIG. 4, the shortened catheter 10' can then be retracted proximally along the guidewire to expose a further length of the catheter. The procedure outlined above may then be repeated as necessary until the entire catheter has been completely removed from the guidewire 20 in a series of discrete segments 14.

The length of the proximal segment 14 an operator cuts away at each step will depend at least in part on the length of the guidewire outside the patient's body P. The longer the portion of the guidewire outside the patient's body, the longer the proximal lengths 14 may be cut, reducing the number of cuts which must be made to completely remove the catheter. Cutting the catheter at a location closer to the patient's body will also maximize the length of the proximal lengths 14 and minimize the number of cuts which must be made. Care should be taken, though, not to cut the catheter so close to the patient's body that the proximal end 12' of the shortened catheter 10' cannot be securely grasped to retract the catheter.

Any of a wide variety of catheters may thus be removed from a guidewire without necessitating movement of the guidewire in accordance with the invention. In accordance with a further embodiment of the invention, a second catheter may then be placed on the guidewire and threaded into position.

Guidewires can be fairly easily dislodged from their desired position when retracting a catheter proximally over the wire due to friction between the guidewire and the catheter. It is generally more difficult to dislodge a guidewire from its intended position by urging it distally, though. Accordingly, it frequently is not necessary to maintain a grasp on the guidewire when urging a new catheter into position within the body along the guidewire. Hence, a new catheter is inserted in accordance with the invention simply by inserting the proximal end 22 of the guidewire into a distal end of the lumen of the new guidewire and tracking along the guidewire in a conventional manner until the desired position is reached.

Figure 5:
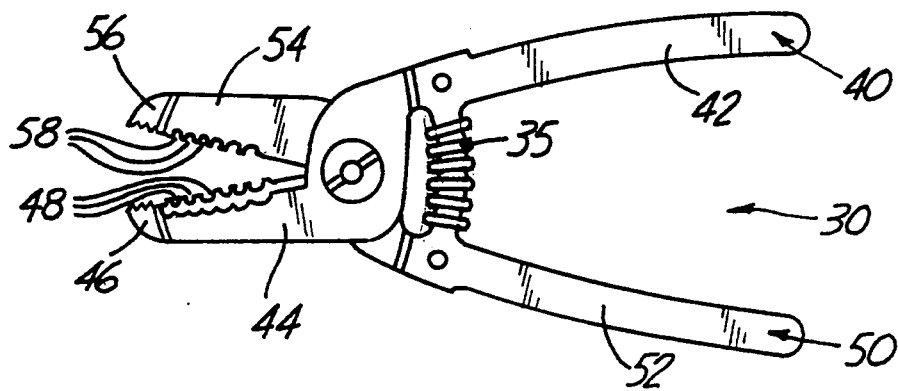
FIG. 5 is a top view of a catheter cutter in accordance with the present invention.
Figure 6:
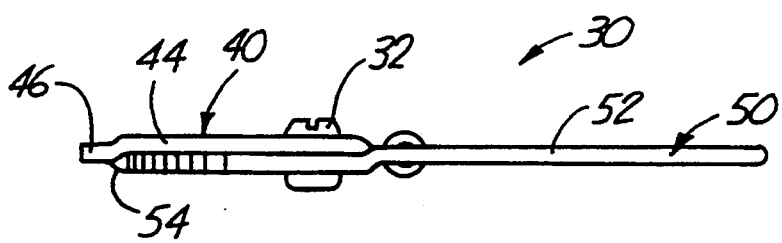
FIG. 6 is a side view of the catheter cutter of FIG. 5.
Figure 7:
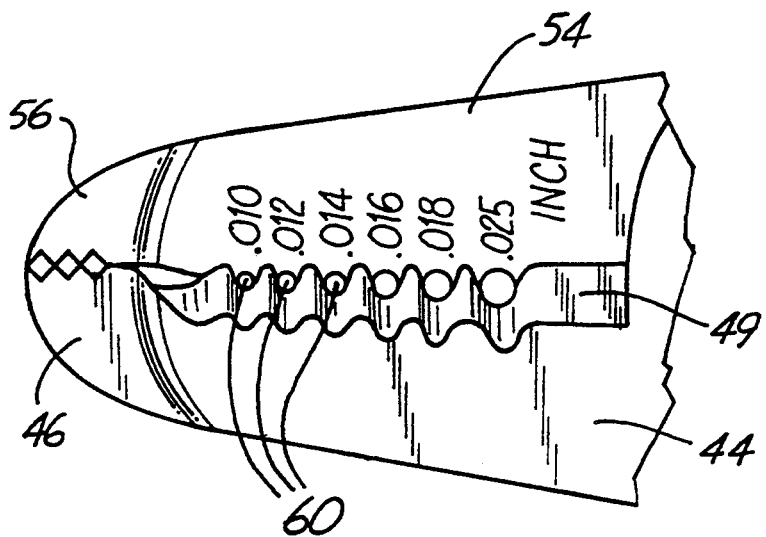
FIG. 7 is a top isolation view of the jaws of the catheter cutter of FIG. 5 wherein the jaws are closed to define a plurality of orifices.

FIGS. 5-7 illustrate a catheter cutter 30 which may be used to cut the catheter 20 in accordance with the method outlined above. The cutter 30 generally includes an upper arm 40 and a lower arm 50, with each arm having a manually graspable leg (42 and 52, respectively) and a forward jaw (44 and 54, respectively). The two arms 40, 50 may be pivotably attached to one another by means of a bolt 32 or the like at a location disposed between the leg and jaw of each arm. This will cause the jaws to be urged toward one another when the manually actuatable legs are urged toward one another by the operator.

In one preferred embodiment, the legs 42, 52 of the catheter cutter 30 are normally biased away from one another, urging the jaws 44, 54 toward their open position, as shown in FIG. 5. As best seen in that figure, this can be accomplished by means of a compression spring 35 which is connected to each leg at a location near the connecting bolt 32. This spring 35 will tend to keep the jaws disposed away from one another unless an operator is urging the jaws closed by manually urging the legs together.

FIG. 7 shows a close-up view of the jaws 44, 54 of the catheter cutter 30 when they are in their closed position, i.e. when the legs are urged toward one another against the biasing force of the spring 35. Each jaw or each leg includes an abutment (e.g. abutment 46 of the top arm) which is adapted to abut the abutment of the other jaw or leg (e.g. abutment 56 of the bottom arm). In the embodiment illustrated, the abutments are disposed at the forward edges of the jaws and comprise short flanges having faces which abut each other in the jaws' closed position.

Each jaw 44, 54 includes at least one notch 48, 58 along its inner surface, i.e. the surface disposed toward the other jaw. When the jaws are in their closed position (shown in FIG. 7), each notch of one jaw is disposed immediately adjacent a corresponding notch in the other jaw, thereby defining an orifice 60 of the catheter cutter 30.

At least one of the jaws 44, 54 is optimally provided with a bevelled edge 49 which provides the inner surface of the notches on that jaw with a sharpened edge. This will make it easier for the cutter 30 to cut through the wall of a catheter in use, as outlined below.

In the embodiment illustrated in FIGS. 5-7, the jaws are not in the same plane. Instead, the jaw 44 of the top arm is disposed above the plane of the jaw 54 of the bottom arm. Hence, when the jaws are in their closed position, the notches 48, 58 of the jaws will not abut against one another but rather the lower surface of the upper jaw 44 will optimally slide along some portion of the upper surface of the lower jaw 54.

The abutment 46, 56 of each arm is bent slightly where it meets the jaw so that these two abutments move in substantially the same plane. These abutments thus serve to stop the jaws as they are urged together, defining the closed position of the jaws an preventing them from being urged so far as to block the orifice(s) 60 in the cutter.

In a preferred embodiment, each jaw has a plurality of notches of differing sizes. When the jaws are in their closed position the differently sized notches define a plurality of differently sized orifices. In the illustrated version of the catheter cutter 30, the sizes of each orifice when the jaws are in their closed position is marked adjacent the orifice. In the embodiment of FIGS. 5-7, visible indicia comprising a series of specific diameters, stated in inches, are provided on the upper surface of the lower jaw 54, with the size of the guidewire with which each orifice is to be used being carded next to the orifice.

In this particular embodiment, the orifice is slightly larger than the guidewire size marked next to the orifice. This will help ensure that the jaws 44, 54 do not crush or otherwise harm the guidwire's structural integrity. For example, orifices marked with the following guidewire diameters may have the following actual internal diameters:

| Guidewire Diameter Marked on Tool | Actual Diameter of Orifice |
| --- | --- |
| 0.010" | 0.0115" |
| 0.012" | 0.0135" |
| 0.014" | 0.0155" |
| 0.016" | 0.0175" |
| 0.018" | 0.0195" |
| 0.025" | 0.0265" |

This provides about 1.5 mils clearance between the orifice and the guidewire, which should be sufficient clearance to allow for manufacturing tolerances in both the guidewire and the orifice of the present invention.

FIGS. 5–7 show the visible indicia in terms of inches, but it is to be understood that any other commonly accepted guidewire sizing convention, such as French size, could instead be used. If so desired, more than one sizing convention could be used. For example, the size of an orifice in one sizing convention may be carried on one surface of a jaw while the size of the orifice in another sizing convention can be marked on the opposite surface of the same jaw (e.g. on the lower surface of the lower jaw 54) or on a surface of the other jaw.

As noted above, in accordance with the invention an operator may use the catheter cutter 30 of the invention to cut a proximal length 14 of a guidewire 10 away from the rest of the catheter 10. The operator will generally know the size of the guidewire being used in the procedure. By looking at the visible indicia carried on the tool, the operator can select the appropriate orifice to use in removing a catheter from about the guidewire being used in that procedure. If the visible indicia are stated in terms of the guidewire intended to be received in a particular orifice, the operator need only look for the appropriate guidewire size on the catheter cutter. If the visible indicia are instead stated in terms of the size of the orifice itself, the operator can select an orifice at least as large as the diameter of the guidewire being used, and preferably slightly larger than the outer diameter of the guidewire.

Once the operator has selected the proper orifice based on a correlation between the guidewire being used and the visible indicia adjacent the orifices 60 of the catheter cutter 30, the jaws of the catheter cutter may be positioned about the catheter and guidewire. Obviously, in order to get the catheter and guidewire between the jaws 44, 54, the jaws will have to be in their normally open position, as illustrated in FIG. 5. Once the notches 48, 58 which define the selected orifice are properly positioned with respect to the catheter and guidewire, the jaws may be urged together by manually urging the legs 42, 52 together against the biasing force of the spring 35. This will cause the jaws to close about the catheter and guidewire toward the position shown in FIG. 7.

As the jaws of the catheter cutter close about the catheter, the notches defining the selected orifice will tend to cut through the tubular wall of the catheter. Once the jaws reach their fully closed position wherein the abutments 46, 56 engage one another, the notches 48, 58 will have substantially cut through the entire thickness of the catheter wall. Since the orifice 60 is selected to correspond to the size of the guidewire being used, the guidewire will fit within the orifice without being unduly compressed by the jaws of the cutter.

This helps maintain the integrity of the guidewire. If the catheter cutter did not include an appropriately sized orifice, the process of cutting the catheter with the cutter 30 would be less effective. If the orifice were unduly large, the catheter may not be completely cut. If the orifice were notably smaller than the outer diameter of the guidewire, the guidewire could become marred. Such marring would not only increase friction between the guidewire and the catheter, but it may also cause a structural weakness in the guidewire which could cause the guidewire to break during further use.

If the guidewire were to break, a distal portion of the wire could become detached in the patient's body, presenting a risk to the patient. For this reason, as well as the convenience of using the present catheter cutter 30, using the catheter cutter of the invention rather than some other tool, such as a scalpel, is preferred in the method of the invention.

The catheter cutter 30 of the invention can be made of any material which is sufficiently hard to reliably cut through the thickness of a catheter wall. For instance, the catheter cutter may be made of a hard plastic material and could be discarded after a single use. In a preferred embodiment, though, the catheter cutter is formed of a more durable material which can be sterilized with existing equipment so it can be used in a number of procedures. Surgical stainless steel has been found to work well in this application.

In previous attempts to solve the problems associated with catheter exchanges noted above, either the catheter or the guidewire were specifically designed to allow the exchange. For instance, most guidewires intended for use with an exchange wire include structure on their proximal end to allow them to be mated to the distal end of the exchange wire. Alternatively, the Baxter catheter noted above includes a special seam along its length which allows the catheter to be split by the guidewire.

The catheter and the guidewire used in the present invention, though, may be of virtually any desired type. As explained above, the catheter is cut into a series of segments and can therefore be removed from the guidewire without necessitating any extension of the guidewire or any special features of the catheter; so long as the catheter can be cut with an appropriate tool (e.g. catheter cutter 30), the method of the invention can be used without regard to the nature of the catheter initially employed. This is particularly advantageous in that an operator who does not realize that a different catheter is needed until after the first catheter is in place can readily exchange the catheter without having to have used a particular guidewire or catheter at the beginning of the procedure.

While a preferred embodiment of the present invention has been described, it should be understood that various changes, adaptations and modifications may be made therein without departing from the spirit of the invention and the scope of the appended claims.

What is claimed is:

1. A method of removing a catheter from about a guidewire without necessitating movement of the guidewire comprising the steps of:
   a. manually grasping a portion of the guidewire which extends proximally of a proximal end of the catheter;
   b. cutting through the wall of the catheter to sever a proximal length of the catheter from the rest of the catheter; and
   c. removing said severed proximal length from about the guidewire.

2. The method of claim 1 wherein the severed proximal length is removed from about the guidewire by sliding the proximal length proximally along the guidewire to define a gap between the severed proximal length and the rest of the catheter, and grasping a portion of the guidewire exposed in said gap.

3. The method of claim 1 wherein steps a–c of claim 1 are repeated to sever a second proximal length from the catheter.

4. The method of claim 1 wherein steps a–c are repeated to sever the entire length of the catheter into a series of discrete proximal lengths to remove the entire length of the catheter from a position about the guidewire.

5. The method of claim 4 further comprising the step of advancing a second catheter over the guidewire after removing the first catheter.

6. A method of removing a catheter from about a guidewire without necessitating movement of the guidewire comprising the steps of:
   a. providing a catheter cutting device which comprises a pair of manually actuatable legs operatively connected to a pair of opposed jaws, each of the jaws including at least one notch, the notches of the jaws together defining at least one orifice for receiving the guidewire;
   b. manually grasping a portion of the guidewire which extends proximally of a proximal end of the catheter;
   c. closing the jaws of the catheter cutting device about the guidewire to dispose the guidewire within the orifice and to cut through the wall of the catheter to sever a proximal length of the catheter from the rest of the catheter; and
   d. removing said severed proximal length from about the guidewire.

7. The method of claim 6 wherein the catheter cutter further comprises a plurality of pairs of opposed notches on the jaws which together define a plurality of differently sized orifices when the jaws are in their closed position, further comprising the step of selecting an orifice of the catheter cutter sized to safely receive the guidewire yet serve to sever the proximal length of the catheter.

8. The method of claim 6 wherein the cut to sever the proximal length of the catheter is oriented generally perpendicularly to the axis of the guidewire.

* * * * *